United States Patent

Cleare et al.

[11] 4,235,868
[45] Nov. 25, 1980

[54] STAINING WITH NITRIDO-BRIDGED OSMIUM OR RUTHENIUM COMPOUNDS

[75] Inventors: Michael J. Cleare; Paul C. Hydes, both of Reading, England

[73] Assignee: Johnson, Matthey & Co., Limited, London, England

[21] Appl. No.: 11,666

[22] Filed: Feb. 12, 1979

[30] Foreign Application Priority Data

Feb. 13, 1978 [GB] United Kingdom ............... 5624/78
May 23, 1978 [GB] United Kingdom ............. 21358/78

[51] Int. Cl.$^3$ ............................................. G01N 1/30
[52] U.S. Cl. ......................................... 424/3; 424/7; 424/8
[58] Field of Search ............... 423/351, 395, 462, 463; 424/3, 7, 8

[56] References Cited

U.S. PATENT DOCUMENTS 4,100,158  7/1978  Hydes et al. ..................... 424/3 X

OTHER PUBLICATIONS

Griffith et al. J. Chem. Soc., Dalton Trans., 1973 pp. 1315-1320.
Cleare et al., J. Chem. Soc. (A) 1970 pp. 1117-1125.
Belova J. Inorganic Chem., USSR, vol. III, No. 9, 1958 pp. 2016-2023.
Milas et al., JACS, vol 81, No. 22, Nov. 20, 1959 p. 6089.
Sterling, Chem. Abs. vol. 72, 1970 Ab. No. 104915e.
Hanker et al., Science, vol. 152, Jun. 17, 1966, pp. 1631-1634.
Hanker et al., Science, vol. 146, Nov. 20, 1964, pp. 1039-1043.
Hanker et al., Electron Micro. Soc. of Amer. Proceed. vol. 33, 1975, pp. 456-457.

*Primary Examiner*—Anna P. Fagelson
*Attorney, Agent, or Firm*—Cushman, Darby & Cushman

[57] ABSTRACT

This invention relates to the staining of cells, and in particular provides a novel reagent for the detection, for example, of DNA (deoxyribonucleic acid) and polysaccharides by electron microscopy.

A reagent for staining cells in accordance with the present invention comprises an aqueous solution of a nitrido-bridged complex of osmium or ruthenium and having the general formula:

$$[M_2^{IV}N(NH_3)_{8-2x}X_{5-y}(H_2O)_x]Y_y.$$

where M represents either Os or Ru, X and Y are the same or different anions selected from nitrate, halide and pseudohalide, x is 0 or 1 and y is 2 or 3.

4 Claims, No Drawings

STAINING WITH NITRIDO-BRIDGED OSMIUM OR RUTHENIUM COMPOUNDS

This invention relates to the staining of cells, and in particular provides a novel reagent for the detection, for example, of DNA (deoxyribonucleic acid) and polysaccharides by electron microscopy.

In the technique of electron microscopy, previously-prepared biological specimens are commonly reacted with a staining reagent in order to increase the differential electron scattering power of the specimen constituents. In other words, the contrast of the electron micrograph of the specimen is increased. Particular reagents are known to stain particular compounds or classes of compound; for example, phosphotungstic acid is a cationic stain and tends to bind to proteins, whereas uranyl acetate is an anionic stain and is reasonably selective for nucleic acids and, to a lesser extent, proteins.

One reagent which is known to be specific for deoxyribonucleic acid (DNA) is a so-called "Feulgen" stain. The reagent is generally a Schiff's reagent which reacts with aldehyde groups liberated by hydrolysis of tissue hydroxyl groups from DNA. Typically, however, reagents of the Schiff's type give only a low contrast or give irregular results and are, therefore, unsuitable for routine work.

One reagent that has been proposed to improve on the traditional Feulgen stains for detection of DNA, and which is also active for the detection of polysaccharides by a PAS-type reaction is so-called "osmium ammine". This is a black crystalline powder which appears to show reproducible staining properties but whose structure is uncharacterised, it being apparently a mixture of compounds. In use, specimens are prepared in the usual way as far as fixation and embedding are concerned and thin sections are then submitted to mild acid hydrolysis before being floated on a solution of the reagent in water through which $SO_2$ has been passed. The reagent concentration, temperature and duration of the staining reaction are variable and selected according to the desired intensity and grain fineness for a given specimen.

It is an object of the present invention to provide a novel staining reagent which is at least equal in performance to "osmium ammine" and which is easy to prepare and characterise.

According to a first aspect of the invention, a reagent for staining cells comprises an aqueous solution of a nitrido-bridged complex of osmium or ruthenium.

According to a second aspect of the invention, a method for staining cells of a prepared biological specimen (as hereinbefore defined) comprises submitting said specimen firstly to mild acid hydrolysis and secondly to reaction with a staining reagent comprising an aqueous solution of a nitrido-bridged complex of osmium or ruthenium.

The general formula of the nitrido-bridged complex is $$[M_2{}^{IV}N(NH_3)_{8-2x}X_{5-y}(H_2O_x)]Y_y$$

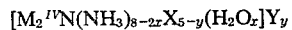

where M represents either Os or Ru, X and Y are the same or different anions selected from nitrate, halide and pseudohalide, x is 0 or 1 and y is 2 or 3.

A pseudohalide is an anion of a pseudohalogen and is defined in "Advanced Inorganic Chemistry" by F. A. Cotton and G. Wilkinson, 2nd Edition, p.560, as being a molecule consisting of more than two electronegative atoms which, in the free state, resembles the halogens, the most important being $(CN)_2$ cyanogen, $(SCN)_2$ thiocyanogen, $(SeCN)_2$ selenocyanogen and $(SCSN_3)_2$ azidocarbondisulphide. In addition there are the azide $N_3{}^-$ and cyanate $OCN^-$ ions which have no pseudohalogen parent. The pseudohalides which we prefer to use in reagents according to the present invention are azide and, not mentioned in the above list, isothiocyanate $NCS^-$.

Three classes of complex which we prefer to use in reagents according to the invention are $[Os_2N(NH_3)_8X_2]Y_3$, $[Ru_2N(NH_3)_8X_2]Y_3$ and $[Ru_2N(NH_3)_6X_3(H_2O)]Y_2$, where X and Y are anions as defined above. Complexes of the first type where X and Y are chloride may conveniently be prepared by heating concentrated ammonia solution with sodium chloroosmate or $K_3[Os_2NCl_8(H_2O)_2]$ in a sealed reaction vessel and reacting the product with concentrated hydrochloric acid, and complexes of the first type where X and Y are anions (either the same or different) other than chloride may readily be prepared from the chloride analogues. Complexes of the second type where X and Y are chloride may be prepared by adding a solution of $K_3[Ru_2NCl_8(H_2O)_2]$ to boiling concentrated aqueous ammonia and reacting the product with concentrated hydrochloric acid and complexes of the third type where X and Y are chloride may be prepared from the mother-liquor from the preparation of complexes of the second type. Complexes of both the second and third type where X and Y are anions (either the same or different) other than chloride may be prepared either by a method similar to that for the preparation of the chloride analogues or directly from the said chloride analogues.

Reagents according to the first aspect of the invention comprise a solution of a nitrido-bridged complex of ruthenium or osmium in distilled water. Typically, the concentration of such a staining solution is 1 mg of complex per milliliter of distilled water. The staining solution may be treated by bubbling $SO_2$ gas through it, typically for 5 minutes before use. This treatment is particularly applicable for staining polysaccharides.

Specimens are typically prepared for staining by fixing in Karnovsky fixative, a mixture of glutaraldehyde and formalin, dehydrating and embedding without osmium post fixing. Thin sections (10 mm) are cut and mounted on gold grids. Alternatively, blocks of tissue may be fixed, hydrolysed and stained before embedding and sectioning.

A typical procedure for staining polysaccharides comprises a first hydrolysis step in which a section of the specimen, prepared by fixing and sectioning as above, is floated on a solution of 1% periodic acid for one hour, a second washing step in which the hydrolysed specimen is washed twice in distilled water, each wash being of five minutes' duration, and a third staining step in which the washed specimen is submerged in the staining solution, preferably pre-treated with $SO_2$, for one hour. The specimen, after a final wash in distilled water, is then ready for examination in the electron microscope.

The procedure for staining DNA is typically to fix small blocks (1 mm³) of tissue in Karnovsky fixative for 1½ hours and wash them in distilled water. The blocks are then hydrolysed with 6 N HCl for 45 minutes, washed twice in distilled water and submerged in the staining solution for 1 hour. The blocks are then washed in distilled water, dehydrated and embedded, and their sections are cut for examination without further staining. The staining solution need not be treated with $SO_2$.

The preparation of complexes forming reagents according to the invention will now be described by way of example, followed by testing results in the staining of glycogen and DNA compared to the performance of osmium ammine.

PREPARATION OF THE COMPLEXES

Di-chloro-octa-ammine μ-nitrido di-osmium (IV) trichloride $[Os_2N(NH_3)_8Cl_2]Cl_3$ Method 1

Concentrated ammonia solution (0.880; 20 ml) was added to $Na_2[OsCl_6]$ (2 g) in a Carius tube and the solution was heated to 100° C. for twelve hours. The resulting yellow solution was filtered and the black precipitate washed with cold dilute aqueous ammonia until the washings were colourless. The washings and filtrate were combined, evaporated to half bulk on the steam bath, cooled, and concentrated hydrochloric acid (10 ml) added to precipitate the product. This was washed with 2 N hydrochloric acid and reprecipitated from aqueous solution with more acid. Yield of yellow crystals 55%.

Method 2

Concentrated ammonia (0.880; 5 ml) was added to a solution of $K_3[Os_2NCl_8(H_2O)_2]$ (0.3 g) and the mixture heated to 100° C. in a sealed Carius tube for twelve hours. The yellow solution was treated as before. The yield was virtually quantitative. The product from both these methods appeared to be a dihydrate; the water could be removed by heating in vacuo to 80° C.

Found for dihydrate: N: 17.4; Cl: 23.5; Os: 50.5%. $H_{28}N_9O_2Cl_5Os_2$ requires N: 16.9; Cl: 23.8; Os: 51.5%.

Found for the anhydrous complex: N: 18.4; Cl: 24.6%. $H_{24}N_9Cl_5Os_2$ requires N: 17.8; Cl: 25.1%.

Electronic spectrum: 265 mμ(shoulder: $\epsilon=1.3\times10^4$); 242 mμ($\epsilon=4.9\times10^4$); ~190 mμ ($\epsilon=0.7\times10^4$).

Magnetic susceptibility: $Xg=-2.8\times10^{-7}$ cgsu (20° C.)

Molar Conductivity:
Initial values:
 $1.34\times10^{-3}$ M; 350 ohm$^{-1}$ cm$^2$
 $4.92\times10^{-4}$ M; 390 ohm$^{-1}$ cm$^2$
 $1.03\times10^{-4}$ M 415 ohm$^{-1}$ cm$^2$
Final value on standing: 530 ohm$^{-1}$ cm$^2$.

Complexes of the form $[Os_2N(NH_3)_8X_2]X_3$ (X=Cl, Br, I, NCS, $N_3$ $NO_3$)

These were prepared in high yield by refluxing an aqueous solution of $[Os_2N(NH_3)_8Cl_2]Cl_3$ with an excess of the potassium or sodium salt of X$^-$ for about one hour. The products are all yellow or yellow-brown.

$[Os_2N(NH_3)_8Br_2]Br_3$—Found H: 2.9; Br: 43.6; N: 14.3%. $H_{24}N_9Br_5Os_2$ requires H: 2.6; Br: 43.0; N: 13.6%.

Magnetic susceptibility: $Xg=-2.7\times10^{-7}$ c.g.s.u. (20° C.)

Electronic spectrum: 272 mμ(sh) ($\epsilon=18,100$); 245 mμ($\epsilon=49,800$); 197 mμ($\epsilon=58,550$)

$[Os_2N(NH_3)_8I_2]I_3$ Found N: 10.5; I: 54.4%. $H_{24}N_9I_5Os_2$ requires N: 10.8; I: 54.5.

$[Os_2N(NH_3)_8(NCS)_2](NCS)_3$—Found C: 6.4; H: 3.7; N: 23.9%. $C_5H_{24}N_{14}S_5Os_2$ requires C: 7.3; H: 3.0; N: 24.2%.

Magnetic susceptibility: $Xg=-2.4\times10^{-7}$ c.g.s.u.

Electronic spectrum: 285 mμ($\epsilon=78,860$)—due to NCS$^-$; 240 mμ(sh) ($\epsilon=21,140$); 194 mμ($\epsilon=36,120$).

Molar conductivity: $1.21\times10^{-4}$M 330 ohm$^{-1}$ cm$^2$.

$[Os_2N(NH_3)_8(N_3)_2]$ $(N_3)_3$—Found H: 3.8; N: 44.5%. $H_{24}N_{24}Os_2$ requires H: 3.3; N: 45.4%.

$[Os_2N(NH_3)_8(NO_3)_2]$ $(NO_3)_3$ was made by dissolving $[Os_2N(NH_3)_8Cl_2]Cl_3$ in the minimum amount of hot water and adding excess silver nitrate to the solution. Dilute nitric acid was then added and the solution boiled to coagulate the silver chloride. The solution was then filtered into excess ethanol; the precipitate thus formed was dissolved in warm water and reprecipitated with concentrated nitric acid. The product formed deep yellow crystals. (Yield 40%).

Found: N: 24.1; O: 27.6%. $H_{24}N_{14}O_{15}Os_2$ requires N: 23.3; O: 28.5%.

Complexes of the form $[Os_2N(NH_3)_8X_2]Y_3$ (XorY=Br$^-$, I$^-$, NCS$^-$, $N_3^-$, $NO_3^-$)

These complexes may be prepared by the addition of a strong aqueous solution of the sodium or potassium salt of Y$^-$ to a cold aqueous solution of $[Os_2N(NH_3)_8X_2]X_3$ in the presence of a small amount of X$^-$. The solubility of $[Os_2N(NH_3)_8X_2]X_3$ is often low in the presence of X$^-$ but if the methathesis is carried out without the latter, there is a danger of some Y$^-$ becoming co-ordinated. Examples of the many complexes covered by this general method are:

$[Os_2N(NH_3)_8Cl_2]I_3$—Found N: 12.7; Os: 36.4%. $H_{24}N_9Cl_2I_3Os_2$ requires N: 12.7; Os: 38.6%.

$[Os_2N(NH_3)_8Cl_2](NCS)_3$—Found C: 4.6; N: 22.0; Cl: 10.0%. $H_{24}C_3N_{12}Cl_2S_3Os_2$ requires C: 4.6; N: 21.7; Cl: 9.1%.

$[Os_2N(NH_3)_8Cl_2]Br_3$—Found N: 15.2; Br: 32.9; Cl: 5.0%. $H_{24}N_9Cl_2Br_3Os_2$ requires N: 15.0; Br: 28.5; Cl: 8.4%.

$[Os_2N(NH_3)_8(N_3)_2]I_3$—Found N: 20.8; I: 37.9%. $H_{24}N_{15}I_3Os_2$ requires N: 21.1; I: 38.2%.

$[Os_2N(NH_3)_8(NO_3)_2]Cl_3$—Found N: 20.3; Cl: 13.6%. $H_{24}N_{11}Cl_3O_6Os_2$ requires N: 20.3; Cl: 14.0%.

$[Os_2N(NH_3)_8(NCS)_2]Cl_3$—Found N: 20.8; C: 3.5; Cl: 13.8%. $H_{24}C_2N_{11}S_2Cl_3Os_2$ requires N: 20.5; C: 3.2; Cl: 14.1%.

Di-chloro-octa-amineμ-nitrido diruthenium (IV) trichloride $[Ru_2N(NH_3)_8Cl_2]Cl_3$ A concentrated aqueous solution of $K_3[Ru_2NCL_8(H_2O)_2]$(2 g. in 20 mls. water) was slowly added to boiling aqueous ammonia (0.880–500 mls.). The turbid solution was filtered to remove a brown precipitate and the filtrate evaporated to low bulk (~50 ml). Concentrated hydrochloric acid (5 mls.) was added to the cold solution and the product separated out as pale orange microcrystals from an orange-red mother liquor. The latter was retained for the isolation of $[Ru_2N(NH_3)_6Cl_3(H_2O)]Cl_2$ The orange crystals of $[Ru_2N(NH_3)_8Cl_2]Cl_3$ were purified by dissolving in hot water and reprecipitating from the cold solution with concentrated NCl. Yield 30%.

Found: H: 4.9; N: 23.6; Cl: 33.2; Ru: 38.0%. $H_{24}N_9Cl_5Ru_2$ requires H: 4.6; N: 23.8; Cl: 33.5; Ru: 38.2%.

Magnetic susceptibility: $Xg=-3.8\times10^{-7}$ c.g.s.u. (20° C.)

Electronic spectrum: 320 mμ($\epsilon=1,440$), 265 mμ($\epsilon=32,020$).

235 mμ(sh) ($\epsilon=9,550$), 200 mμ($\epsilon=21,710$).

Molar conductivity: Initial values varied with concentration as follows:

$0.98 \times 10^{-4}$ M; 395 ohm$^{-1}$ cm$^2$.
$3.51 \times 10^{-4}$ M; 356 ohm$^{-1}$ cm$^2$.
$3.85 \times 10^{-4}$ M; 320 ohm$^{-1}$ cm$^2$.
$9.86 \times 10^{-4}$ M; 305 ohm$^{-1}$ cm$^2$.

Long standing molar conductivity rises to ~570 ohm$^{-1}$ cm$^2$.

Trichloroaquo-hexammino μ-nitrido diruthenium (IV) dichloride [Ru$_2$N(NH$_3$)$_8$Cl$_3$(H$_2$O)]Cl$_2$ The orange-red mother liquor from the preparation of [Ru$_2$N(NH$_3$)$_8$Cl$_2$]Cl$_3$ was evaporated to low bulk and cooled to yield deep orange crystals of the product. This was purified either by reprecipitation from a strong aqueous solution by the addition of concentrated HCl or by recrystallisation from a weaker solution containing HCl.

Found: H: 3.6; O: 3.0; N: 19.4; Cl: 34.2; Ru: 39.1%. Calculated: H: 3.9; C: 3.1; N: 19.1; Cl: 34.5; Ru: 39.4%.

Magnetic susceptibility: $X_g = -2.0 \times 10^{-7}$ c.g.s.u. (21° C.)

Electronic spectrum: 320 mμ($\epsilon = 1{,}500$); 264 mμ($\epsilon = 30{,}540$)
225 mμ($\epsilon = 11{,}240$); 195 mμ($\epsilon = 24{,}200$).

Conductivity:
Initial values:
$1.15 \times 10^{-4}$ M; 274 ohm$^{-1}$ cm$^2$.
$2.11 \times 10^{-4}$ M; 308 ohm$^{01}$ cm$^2$.

Final value after overnight standing: ~500 ohm$^{-1}$ cm$^2$.

Dibromo-octa-ammino μ-nitrido di-ruthenium (IV) tribromide [Ru$_2$N(NH$_3$)$_8$Br$_2$]Br$_3$ This was made in the same way as the chloro derivative but using K$_3$[Ru$_2$NBr$_8$(H$_2$O)$_2$] and hydrobromic acid. Yield 30% of orange crystals.

Found: N: 16.4; Br: 53.7; Ru: 26.6% H$_{24}$N$_8$Br$_5$Ru$_2$ requires N: 16.8; Br: 53.1; Ru: 26.9%.

Magnetic susceptibility: $X_g = -3.1 \times 10^{-7}$ c.g.s.u. (21° C.)

Molar conductivity:
$0.96 \times 10^{-4}$ M Initial value 420 ohm$^{-1}$ cm$^2$.
$1.13 \times 10^{-4}$ M Initial value 400 ohm$^{-1}$ cm$^2$.
After long standing: ~640 ohm$^{-1}$ cm$^2$.

A small amount of [Ru$_2$N(NH$_3$)$_6$(H$_2$O)Br$_3$]Br$_2$ was obtained by working up the mother liquor, but the major yield was brown crystals of a more substituted complex which appears to be Ru$_2$N(NH$_3$)$_4$Br$_5$(H$_2$O). Analytical and conductivity data do not provide a definite distinction between the species [Ru$_2$N(NH$_3$)$_4$Br$_5$(H$_2$O)] and [Ru$_2$N(NH$_3$)$_4$Br$_4$(H$_2$O)$_2$] Br. However, the conductivity was high, even when the measurement was made immediately after the solution had been prepared. This suggested that the nitrate groupsters very weakly bonded to the metal and very labile in solution. The latter was confirmed by the addition of excess X$^-$ (X=I,NCS) to a warm aqueous solution of [Ru$_2$N(NH$_3$)$_8$(NO$_3$)$_2$] (NO$_3$)$_3$ (no further heating was involved). The crystalline precipitates obtained analysed as octammine rather than hexammine complexes. This is a useful means of preparing substituted octammine species, especially those such as the thiocyanato complex which readily forms a hexammine.

[Ru$_2$N(NH$_3$)$_8$I$_2$]I$_3$ Found H: 2.5; N: 13.2; I: 62.9%. H$_{24}$N$_9$I$_5$Ru$_2$ requires H: 2.8; N: 12.6; I: 64.5%.

[Ru$_2$N(NH$_3$)$_8$(NCS)$_2$] (NCS)$_3$—Found C: 10.5; H: 3.9; N: 31.5%. C$_5$H$_{24}$N$_{14}$S$_5$Ru$_2$ requires C: 9.4; H: 3.7; N: 30.5%.

Complexes of the form [Ru$_2$N(NH$_3$)$_8$X$_2$]Y$_3$ (X=Cl, Br; Y=Br, I, NCS, N$_3$, NO$_3$, NO$_2$) were made by the addition of a cold aqueous solution of [Ru$_2$N(NH$_3$)$_8$X$_2$]X$_3$ containing a small amount of X$^-$ to a strong solution of the potassium salts of Y$^-$.

EXAMPLES

[Ru$_2$N(NH$_3$)$_8$Cl$_2$] (NCS)$_3$—Found: H: 4.5; C: 5.8; Cl: 11.9; N: 27.8%. H$_{24}$C$_3$N$_{12}$S$_3$Cl$_2$Ru$_2$ requires H: 4.1; C: 6.0; Cl: 11.9; N: 28.1%.

The former is preferred on the grounds of the low solubility (water) and relatively low conductivity (this may be due to hydrolysis or aquation).

Found: N: 9.9; Br: 55.7%. H$_{14}$N$_5$OBr$_5$Ru$_2$ requires N: 10.0; Br: 56.9%. H$_{16}$N$_5$O$_2$Br$_5$Ru$_2$ requires N: 9.7; Br: 55.5%.

Molar conductivity: $0.50 \times 10^{-4}$ M(H$_2$O) 55 ohm$^{-1}$ cm$^2$

Dinitrato octa-ammino μ-nitrido di-ruthenium (IV) trinitrate [Ru$_2$(NH$_3$)$_8$(NO$_3$)$_2$] (NO$_3$)$_3$ An aqueous solution of [Ru$_2$N(NH$_3$)$_8$Cl$_2$]Cl$_3$ was boiled with dilute nitric acid and excess silver nitrate until the silver chloride which forms had coagulated. The solution was filtered and the filtrate boiled once more to remove any excess silver chloride, cooled and filtered into excess ethanol.

The resulting precipitate was filtered, dissolved in water and reprecipitated as orange crystals with concentrated nitric acid. (Yield 60%).

Found: N: 29.4; Ru: 30.1% H$_{24}$N$_{14}$O$_{15}$Ru$_2$ requires N: 29.6; Ru: 30.5%

Electronic spectrum: 254 mμ($\epsilon = 2.3 \times 10^4$) 209 mμ($\epsilon = 7.26 \times 10^4$)

Molar conductivity:
$1.56 \times 10^{-4}$ M soln. 625 ohm$^{-1}$ cm.$^2$
$1.04 \times 10^{-4}$ M soln. 630 ohm$^{-1}$ cm.$^2$
[Ru$_2$N(NH$_3$)$_8$Cl$_2$]I$_3$—Found I: 47.4%. H$_{24}$N$_9$Cl$_2$I$_3$Ru$_2$ requires I: 47.4%.

[Ru$_2$N(NH$_3$)$_8$Cl$_2$] (NO$_3$)$_3$—Found H: 3.8; N: 28.6; Cl: 8.1%. H$_{24}$N$_{12}$O$_9$Cl$_2$Ru$_2$ requires H: 4.2; N: 29.2; Cl: 12.3%. (This was made without the presence of Cl$^-$).

[Ru$_2$N(NH$_3$)$_8$Br$_2$] (NCS)$_3$ Found: C: 4.9; H: 3.6; N: 24.2%. H$_{24}$C$_3$N$_{12}$S$_3$Br$_2$Ru$_2$ requires C: 5.2; H: 3.5; N: 24.5%.

Hexammine complexes

These appear to take the form [Ru$_2$N(NH$_3$)$_6$(H$_2$O)X$_3$]Y$_2$ (X=NCS N$_3$, NO$_2$; Y=Cl, I). They were made by heating an aqueous solution of [Ru$_2$N(NH$_3$)$_8$Cl$_2$]Cl$_3$ with excess of the potassium or sodium salt of X$^-$. The solutions on cooling deposit orange-red crystals of type [Ru$_2$N(NH$_3$)$_6$X$_3$(H$_2$O)]X$_2$ (X=NCS, N$_3$NO$_2$) in good yield.

[Ru$_2$N(NH$_3$)$_6$ (NCS)$_3$(H$_2$O)](NCS)$_2$. Found: C: 8.9; N: 27.6; Ru: 32.2%. H$_2$OC$_5$N$_{12}$OS$_5$Ru$_2$ requires C: 9.6; N: 27.6; Ru: 32.2%.

Magnetic susceptibility: $X_g = -3.7 \times 10^{-7}$ c.g.s.u. (21° C.)

Electronic spectrum:
326 mμ(NCS$^-$band-$\epsilon = 2.9 \times 10^4$);
248 mμ($\epsilon = 2.44 \times 10^4$); 198 mμ($\epsilon = 2.28 \times 10^4$).

Molar conductivity:
$1.04 \times 10^{-4}$ M Initial value 210 ohm$^{-1}$ cm$^2$
$2.01 \times 10^{-4}$ M Initial value 180 ohm$^{-1}$ cm$^2$ After long standing 230 ohm$^{-1}$ cm$^2$.

$[Ru_2N(NH_3)_6(N_3)_3(H_2O)]$ $(N_3)_2$—Found H: 4.0; N: 55.9%. $H_{20}N_{21}ORu_2$ requires H: 3.7; N: 56.4%.

$[Ru_2N(NH_3)_6(NO_2)_3(H_2O)]$ $(NO_2)_2$—found H: 4.3; N: 29.8%. $H_{20}N_{12}O_{11}Ru_2$ requires H: 3.5; N: 29.7%.

Electronic spectrum:
  297 m$\mu$(sh) ($\epsilon = 5.06 \times 10^3$);
  259 m$\mu$($\epsilon = 2.74 \times 10^4$)
  232 m$\mu$(sh) ($\epsilon = 1.73 \times 10^4$);
  208 m$\mu$($\epsilon = 1.76 \times 10^4$).

Addition of a potassium salt of Y$^-$ (Y=Cl, I, NCS) to an aqueous solution of $[Ru_2N(NH_3)_6(H_2O)X_3]X_2$ containing some X$^-$ ion, yield the complexes $[Ru_2N(NH_3)_6H_2OX_3]Y_2$.

$[Ru_2N(NH_3)_6(H_2O)(NCS)_3]Cl_2$—Found C: 6.2; N: 23.4; Cl: 11.6%. $H_{20}C_3N_{10}CS_3Cl_2Ru_2$ requires C: 6.2; N: 24.2; Cl: 12.2%.

$[Ru_2N(NH_3)_6(H_2O)(N_3)_3]Cl_2$—Found N: 41.5; Cl: 13.3%. $H_{20}N_{16}OCl_2Ru_2$ requires N: 41.9; Cl: 13.3%.

$[Ru_2N(NH_3)_6H_2CCl_3](NCS)_2$—Found C: 4.5; H: 3.4; N: 22.7%. $C_2H_2OH_9OCl_3S_2Ru_2$ requires C: 4.3; H: 3.6; N: 22.6%.

$[Ru_2N(NH_3)_6H_2O(NO_2)_3]Cl_2$—Found N: 26.5; Cl: 13.5%. $H_{20}N_{10}O_7Cl_2Ru_2$ requires N: 25.7; Cl: 13.0%.

TEST RESULTS

| Complex | Treatment Compound | Specimen | Staining |
|---|---|---|---|
| Glycogen Staining | | | |
| Osmium ammine | 5 min. SO$_2$ | 1% PA 1hr | 5+ |
| | — | 1% PA 1hr then SO$_2$/H$_2$O 30 min | — |
| | 5 min. SO$_2$ | — | — |
| [Os$_2$N(NH$_3$)$_8$Cl$_2$]Br$_3$ | 5 min. SO$_2$ | 1% PA 1hr | 5+ |

TEST RESULTS (continued)

| Complex | Treatment Compound | Specimen | Staining |
|---|---|---|---|
| | 5 min. SO$_2$ | — | — |
| [Os$_2$N(NH$_3$)$_8$Cl$_2$](NO$_3$)$_3$ | " | 1% PA 1hr | 5+ |
| | — | 1% PA 1hr then SO$_2$/H$_2$O 30 min | 5+ |
| [Os$_2$N(NH$_3$)$_8$Cl$_2$]I$_3$ | | " | 2+ |
| DNA STAINING | | | |
| [Os$_2$N(NH$_3$)$_8$Cl$_2$](NO$_3$)$_3$ | 5 min. SO$_2$ | 6N HCl 1hr | 3+ |

We claim:

1. A method for staining cells of a prepared biological specimen which comprises submitting said specimen firstly to mild acid hydrolysis and secondly to reaction with a staining reagent comprising an aqueous solution of a nitrido-bridged complex of osmium or ruthenium having the general formula $$[M_2^{IV}N(NH_3)_{8-2x}X_{5-y}(H_2O)_x]Y_y$$

where M represents either Os or Ru, X and Y are the same or different anions selected from the group consisting of nitrate, halide and psuedohalide, x is 0 or 1 and y is 2 or 3.

2. A method according to claim 1 wherein the said complex has the formula
  (i) [Os$_2$N(NH$_3$)$_8$X$_2$]Y$_3$,
  (ii) [Ru$_2$N(NH$_3$)$_8$X$_2$]Y$_3$, or
  (iii) [Ru$_2$N(NH$_3$)$_6$X$_3$(H$_2$O)]Y$_2$.

3. A method according to claim 2 wherein X and Y in formula (i) and formula (ii) are chloride.

4. A method according to claim 2 wherein the complex has the formula:
  (iv) [Os$_2$N(NH$_3$)$_8$Cl$_2$]Cl$_3$,
  (v) [Ru$_2$N(NH$_3$)$_8$Cl$_2$]Cl$_3$,
  (vi) [Ru$_2$N(NH$_3$)$_6$Cl$_3$(H$_2$O)]Cl$_3$, or
  (vii) [Ru$_2$N(NH$_3$)$_8$Br$_2$]Br$_3$.

* * * * *